US00PP22377P2

(12) United States Plant Patent
Dümmen

(10) Patent No.: US PP22,377 P2
(45) Date of Patent: Dec. 20, 2011

(54) ***PELARGONIUM* PLANT NAMED 'DUEVISALPI'**

(50) Latin Name: *Pelargonium zonale*
Varietal Denomination: Duevisalpi

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/924,023

(22) Filed: Sep. 17, 2010

(51) Int. Cl.
*A01H 5/00* (2006.01)

(52) U.S. Cl. ..... Plt./327

(58) Field of Classification Search ..... Plt./327
See application file for complete search history.

*Primary Examiner* — Annette Para
(74) *Attorney, Agent, or Firm* — C. A. Whealy

(57) ABSTRACT

A new and distinct cultivar of Zonal Geranium plant named 'Duevisalpi', characterized by its upright to outwardly spreading plant habit; vigorous growth habit; freely basal branching habit; dark green-colored leaves with a distinct zonation pattern; freely flowering habit; semi-double salmon red-colored flowers; and good garden performance.

1 Drawing Sheet

Botanical designation: *Pelargonium zonale.*
Cultivar denomination: 'DUEVISALPI'.

BACKGROUND OF THE INVENTION

The present invention relates to a new and distinct cultivar of Zonal Geranium plant, botanically known as *Pelargonium zonale* and hereinafter referred to by the name 'Duevisalpi'.

The new Zonal Geranium plant is a product of a planned breeding program conducted by the Inventor in Rheinberg, Germany. The objective of the breeding program is to create new vigorous Zonal Geranium plants with dark green-colored leaves and attractive flowers.

The new Zonal Geranium plant originated from a cross-pollination made by the Inventor in December, 2005 in Rheinberg, Germany of a proprietary selection of *Pelargonium zonale* identified as code number F-06-18, not patented, as the female, or seed, parent with a proprietary selection of *Pelargonium zonale* identified as code number F-12-01, not patented, as the male, or pollen, parent. The new Zonal Geranium plant was discovered and selected by the Inventor as a single flowering plant from within the progeny of the stated cross-pollination in a controlled greenhouse environment in Rheinberg, Germany in May, 2009.

Asexual reproduction of the new Zonal Geranium plant by vegetative terminal cuttings in a controlled greenhouse environment in Rheinberg, Germany since May, 2009 has shown that the unique features of this new Zonal Geranium plant are stable and reproduced true to type in successive generations.

SUMMARY OF THE INVENTION

Plants of the new Zonal Geranium have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duevisalpi'. These characteristics in combination distinguish 'Duevisalpi' as a new and distinct cultivar of Zonal Geranium plant:

1. Upright to outwardly spreading plant habit.
2. Vigorous growth habit.
3. Freely basal branching habit.

4. Dark green-colored leaves with a distinct zonation pattern.
5. Freely flowering habit.
6. Semi-double salmon red-colored flowers.
7. Good garden performance.

Plants of the new Zonal Geranium differ primarily from plants of the parent selections in flower color as plants of the female parent selection have red-colored flowers and plants of the male parent selection have pink-colored flowers. In addition, plants of the new Zonal Geranium are more vigorous than plants of the parent selections.

Plants of the new Zonal Geranium can be compared to plants of *Pelargonium zonale* 'Dueimgab', disclosed in U.S. Plant Pat. No. 21,112. In side-by-side comparisons conducted in Rheinberg, Germany, plants of the new Zonal Geranium differed primarily from plants of 'Dueimgab' in flower color as plants of 'Dueimgab' had salmon pink-colored flowers.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant. The photograph comprises a side perspective view of a typical flowering plant of 'Duevisalpi' grown in a container.

DETAILED BOTANICAL DESCRIPTION

The aforementioned photograph and following observations and measurements describe plants grown during the summer in 10.5-cm containers in a glass-covered greenhouse in Rheinberg, Germany and under conditions which closely approximate commercial production. During the production of the plants, day and night temperatures averaged 18° C. and light levels averaged 4,500 lux. Plants were pinched one time three weeks after planting. Plants were 13 weeks old when the photograph and the description were taken. In the detailed description, color references are made to The Royal Horticultural Society Colour Chart, 1995 Edition, except where general terms of ordinary dictionary significance are used.

Botanical classification: *Pelargonium zonale* 'Duevisalpi'.

Parentage:

*Female, or seed, parent.*—Proprietary selection of *Pelargonium zonale* identified as code number F-06-18, not patented.

*Male or pollen parent.*—Proprietary selection of *Pelargonium zonale* identified as code number F-12-01, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching.

Plant description:

*General appearance.*—Upright to outwardly spreading plant habit; uniformly rounded; densely foliated.

*Growth and branching habit.*—Vigorous growth habit; freely basal branching habit with about three basal branches developing per plant; pinching enhances lateral branch development.

*Plant height to top of flower umbels.*—About 21 cm.

*Plant height to top of foliar plane.*—About 15 cm.

*Plant width.*—About 21 cm.

*Lateral branches.*—Length: About 6 cm. Diameter: About 6 mm. Internode length: About 1.3 cm. Texture: Pubescent. Strength: Moderately strong. Color: Close to 144B.

Foliage description:

*Arrangement.*—Alternate; simple.

*Length.*—About 5.1 cm.

*Width.*—About 5.5 cm.

*Shape.*—Reniform.

*Apex.*—Acute.

*Base.*—Cordate.

*Margin.*—Crenate.

*Venation pattern.*—Palmate.

*Texture, upper surface.*—Pubescent.

*Texture, lower surface.*—Smooth, glabrous.

*Color.*—Developing leaves, upper surface: Close to 137A. Developing leaves, lower surface: Close to 137C to 137D. Fully expanded leaves, upper surface: Close to 137A; venation, close to 144A. Fully expanded leaves, lower surface: Close to 137D; venation, close to 143C.

*Zonation pattern.*—Distinct. Distance from margin: About 9 mm. Width: About 8 mm. Color: Close to 165A to 165B.

*Petiole.*—Length: About 6.8 cm. Diameter: About 2.4 mm. Texture, upper and lower surfaces: Smooth, glabrous. Color, upper and lower surfaces: Close to 143A.

Flower description:

*Flower arrangement.*—Semi-double flowers arranged in rounded hemispherical umbels arising from apical leaf axils; umbels displayed above the foliage on moderately strong peduncles; flowers face upright to outward.

*Fragrance.*—Not detected.

*Quantity of flowers.*—Freely flowering habit; about 24 flowers and flower buds per umbel; about 160 to 180 flowers develop per plant.

*Flowering season.*—Year-round under greenhouse conditions; in outdoor nurseries and gardens in Germany flowering is continuous from spring throughout the summer; plants begin flowering about eight weeks after planting.

*Flower longevity.*—Individual flowers last about five to seven days on the plant; flowers persistent.

*Umbel height.*—About 5 cm.

*Umbel diameter.*—About 7.5 cm.

*Flower diameter.*—About 4.5 cm by 4 cm.

*Flower depth (height).*—About 2.1 cm.

*Flower buds.*—Length: About 1.1 cm. Diameter: About 5.8 mm. Shape: Ovoid. Color: Close to 58D.

*Petals.*—Quantity per flower: About five in a single whorl. Length: About 2.1 cm. Width: About 1.7 cm. Shape: Obovate. Apex: Rounded. Base: Attenuate. Margin: Sinuate. Texture, upper and lower surfaces: Smooth, glabrous. Color: When opening and fully opened, upper surface: Close to 57C; color becoming closer to 57B with development. When opening and fully opened, lower surface: Close to 67C and 68D; color becoming closer to 57B with development.

*Petaloids.*—Quantity per flower: About three. Length: About 1.8 cm. Width: About 1.2 cm. Shape: Obovate. Apex: Rounded. Base: Attenuate. Margin: Sinuate. Texture, upper and lower surfaces: Smooth, glabrous. Color: When opening and fully opened, upper surface: Close to 57C. When opening and fully opened, lower surface: Close to 67C and 68D.

*Sepals.*—Quantity per flower: Five arranged in a single whorl. Length: About 1 cm. Width: About 3.4 mm. Shape: Ensiform. Apex: Acuminate. Base: Acute. Margin: Entire. Texture, upper and lower surfaces: Smooth, glabrous. Color, upper surface: Close to 143C tinted with close to 183D. Color, lower surface: Close to 143B tinted with close to 181A.

*Peduncle (umbel stem).*—Length: About 10 cm to 11 cm. Diameter: About 4 mm. Strength: Moderately strong. Texture: Smooth, glabrous. Color: Close to 144A.

*Pedicel (individual flower stem).*—Length: About 2.1 cm. Diameter: About 1 mm to 2 mm. Strength: Moderately strong. Texture: Smooth, glabrous. Color: Close to 144C tinted with close to 183D.

*Reproductive organs.*—Androecium: Stamen quantity per flower: About ten. Filament length: About 6.4 mm. Filament color: Close to 155C and 66B. Anther length: About 2 mm. Anther shape: Oval. Anther color: Close to 179A. Pollen amount: Moderate. Pollen color: Close to 28A. Gynoecium: Pistil quantity per flower: One. Pistil length: About 8 mm. Stigma shape: Parted. Stigma color: Close to 47A. Style length: About 2 mm. Style color: Close to 60C. Ovary color: Close to 144B.

*Seed/fruit.*—Seed and fruit development have not been observed.

Disease/pest resistance: Plants of the new Zonal Geranium have not been observed to be resistant to pathogens and pests common to Zonal Geraniums.

Garden performance: Plants of the new Zonal Geranium have been observed to tolerate rain, wind, and temperatures ranging from about 5° C. to about 40° C. and have demonstrated good garden performance.

It is claimed:

1. A new and distinct Zonal Geranium plant named 'Duevisalpi' as illustrated and described.

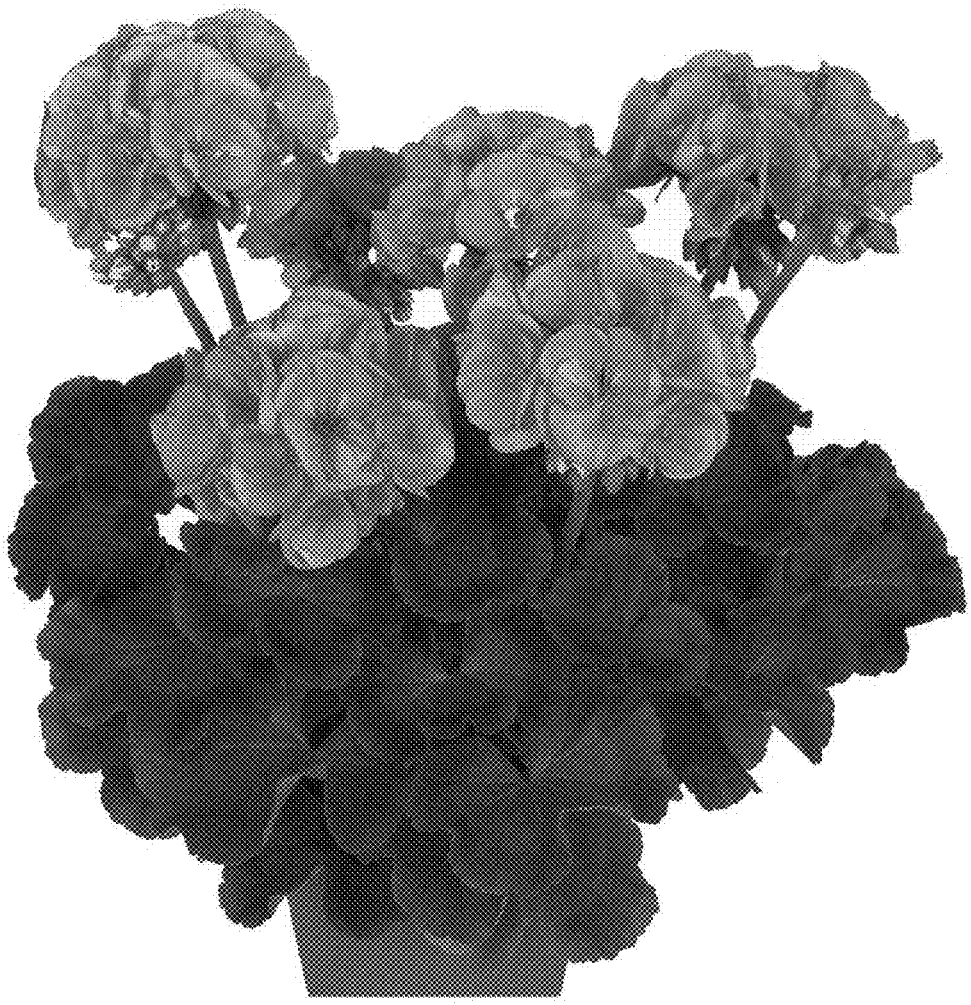

* * * * *